United States Patent [19]

Bryan

[11] Patent Number: 5,122,350
[45] Date of Patent: Jun. 16, 1992

[54] METHOD FOR PREPARING CALCIUM MAGNESIUM ACETATE AND A RESIDUAL MINERAL PRODUCT BY SELECTIVELY CALCINING DOLOMITE

[76] Inventor: William L. Bryan, 6806 N. Aycliffe Dr., Peoria, Ill. 61614

[21] Appl. No.: 545,572

[22] Filed: Jun. 29, 1990

[51] Int. Cl.$^5$ ............................................. C01F 5/16
[52] U.S. Cl. ..................... 423/169; 423/155; 423/173; 423/430; 423/637; 252/70
[58] Field of Search ............... 423/155, 169, 173, 430, 423/637, 635; 252/70; 435/140

[56] References Cited

U.S. PATENT DOCUMENTS

| | | | |
|---|---|---|---|
| 2,155,139 | 4/1939 | MacIntire | 423/169 |
| 4,430,240 | 2/1984 | Sandvig et al. | 252/70 |
| 4,588,512 | 5/1986 | Rippie | 252/70 |
| 4,606,836 | 8/1986 | Gancy | 252/70 |
| 4,636,467 | 1/1987 | Chynoweth | 435/140 |
| 4,699,725 | 10/1987 | Gancy | 252/70 |
| 4,913,831 | 4/1990 | Todd, Jr. et al. | 252/70 |
| 4,935,360 | 6/1990 | Klemps et al. | 435/140 |

OTHER PUBLICATIONS

Ljungdahl et al., "Three Thermophilic Acetogenic Bacteria for Production of Calcium Magnesium Acetate".
Cruger et al., "Textbook of industrial Microbiology".
"Comparison of Three Thermophilic Acetogenic Bacteria for Production of Calcium-Magnesium Acetate" LJUNGDAHL et al., 1986.
"Fermentation as an Advantageous Route for the Production of an Acetate Salt for Roadway De-Icing" MARYNOWSKI et al., 1985.
"Process Development for Production of Calcium Magensium Acetate (CMA)" MARYNOWSKI et al., 1983, pp. 12, 14, 19, 25-27, 42 and 54-55.
"CMA Manufacture [II], Improved Bacterial Strain for Acetate Production," LJUNGDAHL et al., 1986, pp. 19, 37, 65, 68 and 82-84.
*Fluid Mixing Technology*, by James Y. Oldshue, Ph.D., pp. 54 and 55; and 354-355.
"Steam Catalysis in Calcinations of Dolomite and Limestone Fines" (Jul. 1953) by W. H. MacIntire and T. B. Stansel from *Industrial and Engineering Chemistry*, vol. 45, No. 7; pp. 1548-1555.

Primary Examiner—Theodore Morris
Assistant Examiner—Edward Squillante
Attorney, Agent, or Firm—Sixbey, Friedman, Leedom & Ferguson

[57] ABSTRACT

Fermentors, reactors and processes for preparing magnesium enriched calcium magnesium acetate (CMA) (Mg:Ca mole ratios of 1:1 to 20:1) by reacting a dolomitic lime product with a Mg:Ca mole ratio less than one with dilute acetic acid, such as in fermentation broths. A process to prepare a mildly aklaline mineral product by calcining the dolomite under conditions to convert only the $MgCO_3$ to $MgO$ and treating the selectively calcined dolomite with acidic solutions to dissolve largely the $MgO$, leaving the original $CaCO_3$ matrix intact. The mildly alkaline mineral product includes a highly porous structure derived from dolomite, consisting of a matrix of $CaCO_3$ with smaller amounts of $MgO$ and interspersed with a regular array of voids on a molecular scale.

51 Claims, 3 Drawing Sheets

METHOD FOR PREPARING CALCIUM MAGNESIUM ACETATE AND A RESIDUAL MINERAL PRODUCT BY SELECTIVELY CALCINING DOLOMITE

BACKGROUND OF THE INVENTION

An alternate road deicer is needed to replace the nine million tons of salt (NaCl) used annually in the U.S. Although both inexpensive and effective, salt causes enormous economic losses annually from corrosion of vehicles, bridges and underground utilities, from deterioration of concrete roads and bridges, from pollution of streams and water supplies, and from killing roadside vegetation. Pollution of water supplies with NaCl is of particular concern in states such as in Massachusetts, where the sodium content in drinking water in many communities already exceeds 20 mg/L, the recommended upper limit for individuals on a sodium-restricted diet.

As a result of research sponsored by the Federal Highway Administration, calcium magnesium acetate (CMA) has been identified as almost equivalent to salt (NaCl) in deicing properties without the harmful side effects. It is nontoxic, noncorrosive, nonpolluting and has a lower freezing point depression than salt. The freezing point depression is $-23°$ C. for CMA with an equimolar ratio and decreases for mixtures that contain higher ratios of magnesium until the optimum (eutectic) composition is reached at a Mg:Ca mole ratio of approximately 2.3 and a freezing point of $-37°$ C., compared with $-21°$ C. for NaCl. Widespread use of CMA would also help to alleviate the effects of acid rain by acting as a buffer and helping to neutralize sulfuric and nitric acids in the environment adjacent to roadways and in streams and lakes that receive the runoff. CMA has performed satisfactorily in field evaluations, except that a somewhat higher application rate than for NaCl was required for equivalent deicing.

The major deterrent to CMA use is cost. Approximately 80% of CMA manufacturing cost is for acetic acid, which lists for $0.29/lb. plus shipping. For example "ICE-B-GON manufactured by Chevron Chemical Co. from glacial acetic acid, magnesia (MgO) and dolomitic lime products such as dolime (CaO.MgO) or hydrated dolime [Ca(OH)$_2$ . Mg (OH)$_2$], currently costs $0.30/lb. f.o.b. plant for the 91% purity product.

Although the short term cost of deicing with CMA, including the costs of equipment depreciation and labor, may be five to ten-fold higher than for NaCl due to manufacturing costs, the long term savings from CMA use would be much higher than the CMA cost because of reduced damage to water supplies, vehicles, underground utilities, road side vegetation and the nation's highway infrastructure. As a result, the economic and environmental advantages of using CMA would be more effectively realized by lowering the manufacturing costs of CMA.

Two methods have been proposed for reacting acetic acid with calcium and magnesium oxides to prepare CMA. Method I reacts dolomitic lime products [CaO.MgO or Ca(OH)$_2$. Mg(OH)$_2$] and MgO with glacial acetic acid which has been diluted with approximately 10-20% water, needed to help remove the heat released during neutralization and prevent an excessive temperature rise, which might create a safety hazard from the possibility of explosive combustion of acetic acid vapor with air. The CMA product is formed into spherical pellets, as for "ICE-B-GON," and dried to remove most of the residual water. Projected cost, estimated in 1986 for production of 40,000 tons/yr, was $0.215/lb. CMA, based on acetic acid at $0.250/lb. and dolime (CaO.MgO) at $0.045/lb. ($90/ton). The CMA for that study was made with an equimolar Ca:Mg ratio. To produce CMA with a 3Ca:7Mg ratio requires substitution for part of the dolime with magnesia, thereby adding to the projected CMA production cost, size MgO lists for $0.20/lb. plus shipping.

Method II is another plausible and potentially cost-competitive approach to CMA production that has not been commercialized in which dilute acetic acid made by fermentation is neutralized with dolomitic lime products and magnesia, followed by bacterial cell separation, liquid concentration to remove most of the water in multiple-effect evaporators or vapor recompression evaporators, and drying the final product. In this approach, the acetic acid would be made from renewable resources (grains, wood or crop residues) or even from carbon monoxide, carbon dioxide or hydrogen gases. An anaerobic thermophilic microorganism, *Clostridium thermoaceticum* was proposed because the theoretical conversion cf glucose to acetic acid was 100%, with 85% found experimentally. Other thermophilic acetogenic bacteria such as *Clostridium thermoautotroohicum* and *Acetocenium kivui* may also be used. However, these microorganisms cannot tolerate a low pH and their growth rate and rate of production of acetic acid decline drastically as the concentration of free acetic acid increases.

The prior art teaches that pH-controlled *C. thermoaceticum* fermentations with NaOH additions to form sodium acetate increased acetate concentration threefold compared with fermentations without pH control. Commercial success, therefore, would depend on neutralizing the acetic acid to form CMA as soon as it is formed and on cultures that are tolerant to CMA solutions, thus allowing a higher concentration of CMA to be attained in the fermentation broth, which would reduce the amount of water that must be evaporated during the liquid concentration step prior to drying.

Method II can also be applied to fermentation broths of Acetobacter strains to form CMA during the fermentation or in the clarified vinegar resulting from that type fermentation. Acetobacter strains used to make vinegar are more tolerant to acetic acid, but conversion yields are lower, 67% theoretical with 60-65% realized in production. The ret cost to produce CMA by Method II from corn at $2.00/bushel and using either Acetobacter or *Clostridium thermoaceticum* fermentation broths was estimated to be approximately the same, $0.17/lb., because the by-product credits from the vinegar process were more than those from the higher-yielding thermophilic fermentation and more water had to be evaporated in the latter process.

Therefore there is a need for a neutralization process which reduces the costs of producing CMA by reducing the need for MgO in preparing a 2.3 Mg/Ca product.

Also, there exists a need for a less expensive process for effectively manufacturing CMA from fermentation broths while controlling pH within a range for microorganisms to actively grow and produce acetic acid.

There is also a need for a process to reduce the cost of CMA production by use of decentralized processing plants that use locally available raw materials such as corn to produce a concentrated liquid CMA product to serve local areas, thus avoiding the costs of drying, handling and storing a granular solid.

Additionally, a need exists for a process to reduce the cost of CMA production by means of cocurrent production of valuable by-products in addition to corn germ, fiber and animal feed recovered from the milling and fermentation processes which may be sold to help offset the costs of CMA production.

Finally, there is a need for a method to react $MgO \cdot CaCO_3$ with acetic acid solutions in a vertical cascade reaction equipped with rotating mixing elements and separate the $CO_2$ in each stage, thus avoiding the interference from $CO_2$ bubbles rising between stages causing a large amount of $CO_2$ to flood the top of the reactor.

SUMMARY OF THE INVENTION

It is a primary object of the present invention, therefore, to overcome the deficiencies of the prior art discussed above and to provide a cost-effective process for preparing CMA from the neutralization of fermentation broths.

Another object of the present invention is to produce CMA with a Mg:Ca mole ratio greater than 1, while controlling pH within an acceptable range for microorganisms to grow and with minimum risk of raising the pH to a level that is lethal to the microorganisms in the fermentation broth.

A further object of the present invention is to provide a process for preparing magnesium-enriched CMA without the need to use more expensive magnesia to enrich the product.

A still further object of the present invention is to provide a method for producing CMA by reacting the acetic acid in fermentation broths with a selectively calcined and specially treated dolomitic lime product consisting largely of $CaCO_3 \cdot MgO$, followed by cell separation, concentrating the liquid CMA solution and, optionally, drying to a solid product.

Yet another object of the present invention is to provide a method for producing CMA by adding an excess of calcined dolomite to the fermentation broth and separating out the unreacted material to result in CMA solutions with Mg/Ca ratios of more than five during neutralization of the fermentation broth.

Yet another object of the present invention is to provide a method for producing CMA. by using dolomite specifically calcined at a lower temperature and reacted with acetic acid to cause magnesium to dissolve preferentially or at a higher rate than calcium producing a CMA solution enriched in magnesium and a residue enriched in calcium.

Yet another object of the present invention is to provide a method for producing CMA by using calcined dolomite to neutralize the acetic acid solution to prepare CMA with a Mg/Ca mole ratio greater than one with minimum risk of raising pH to a level that is lethal to microorganisms.

Another object of the present invention is to provide a less expensive process to prepare a liquid CMA product than by dissolving the dry solid in water for applications where a liquid product would be more stable in storage and preferable for spreading than a dry solid.

Another object of the present invention is to provide a process to reduce the cost of producing a CMA solid product with a Mg:Ca ratio of 2.3 from glacial acetic acid by substituting for the dilution water needed to reduce overheating, a CMA solution highly enriched in Mg and produced by reacting selectively calcined dolomite, $CaCO_3 \cdot MgO$, with aqueous acetic acid solutions of concentration limited only so as not to exceed the solubility of the CMA formed from the reaction, which precludes separation from the residual insoluble Ca-enriched residue.

Still another object of the present invention is to provide an absorptive and mildly alkaline mineral product with a highly porous structure made from dolomite and consisting of a matrix of $CaCO_3$ substantially as it existed in the rhomohedral crystal structure of the original dolomite mineral interspersed with voids or holes on a molecular scale where a large fraction of the original $MgCO_3$ has been removed.

Another object of the present invention is to provide an absorptive and mildly alkaline mineral product derived from dolomite, which has many applications including acting as: a substitute for agricultural limestone to increase pH of soils at a higher rate than conventional dolomite or limestone; a replacement for certain molecular sieves which cause separations of liquids or gases based on molecular size of the materials to be separated; an adsorbent for acid gases such as $NO_2$ and $SO_2$ emissions present in the exhaust gas of coal-burning power plants or $H_2S$ present in natural gas and refining gas streams; an additive for "kitty litter" to absorb and deodorize animal wastes.

Yet another object of the present invention is to provide a process for preparing a mildly alkaline mineral product derived from dolomite with a porous structure consisting of a matrix of $CaCO_3$, wherein the process includes the steps of: crushing, grinding and classifying the raw dolomite into the desired size ranges, selectively calcining in an atmosphere of humidified $CO_2$ and at a temperature high enough to cause $MgCO_3$ to destruct to MgO and $CO_2$ but low enough that $CaCO_3$ remains largely unaffected, cooling in an atmosphere of humidified $CO_2$ to cause any CaO that formed to be converted to $CaCO_3$, reacting the resultant $CaCO_3 \cdot MgO$ with an acidic solution so as to cause a large fraction of the MgO to be preferentially dissolved, an washing and drying the final product.

A final object of the present invention is to provide an improved reactor or fermentor of the continuous cocurrent liquid-solid dissolver type for implementing the other objects of the present invention, by installing inverted conical baffles at the top of each compartment to reduce the sedimentation of solid particles on the upper surface while providing a space beneath the lower baffle surface to both collect $CO_2$ gas formed from the dissolution of $CaCO_3$ in acetic acid and separate the $CO_2$ gas from the liquid, thus allowing the dissolution reactions to proceed smoothly in each compartment without interference of $CO_2$ gas bubbles rising and causing a multitude of bubbles to flood the top of the reactor/fermentor.

DETAILED DESCRIPTION OF THE INVENTION

The process of forming calcium magnesium acetate (CMA) from the neutralization of fermentation broths uses a selectively calcined dolomite to modify reactivity and cause magnesium to dissolve preferentially or at a higher rate than calcium. In this process, an excess of the selectively calcined dolomite is added to the broth and unreacted material is separated. This approach has resulted in CMA solutions with Mg/Ca ratios of more than five during neutralization of simulated fermentation broths and provides a guide for use in actual fermentations.

Selectively calcined dolomite is a known product wherein dolomite has undergone selective calcination. Such calcination in air normally occurs at temperatures within the range of between 720° and 770° C., with 725° C. being a preferred temperature, for periods within the range of from one to three hours. Selective calcination of dolomite in inert gases and steam lowers the required temperature range to between 550° to 650° C.

The fermentation broths used in accordance with this invention may incorporate nutrients and substrates made from raw materials available in large quantities formed from renewable resources such as lignocellulose crops, grains, woods and agricultural residues. These raw materials are converted to nutrients such as glucose and other sugars in known manner with liquid (i.e., water) to form a broth to which are added fermentation producing microorganisms. Other substrates in the form of CO, $CO_2$ and $H_2$ gases may also be added continuously to the broth, which also act to maintain anaerobic conditions for thermophilic fermentations. Thermophilic acetogenic bacteria which convert glucose to acetic acid are effective for the purpose of this invention, but acetobacter strains commonly used to produce vinegar may also be used. Microbial strains such as *Clostridium thermoaceticum, Clostridium thermoautotroohicum* and *Acetocenium kivui* have been found to be effective fermentation microorganisms that produce acetic acid in small concentrations, but their growth is increasingly inhibited as the acid content builds up in the fermentation broth.

For Acetobacter fermentations, ethanol is the substrate and gaseous oxygen or air must be continuously added for acetic acid to be formed. Growth of Acetobacter is also inhibited by acetic acid and this invention is intended to be applicable for production of CMA in the vinegar process.

For optimum acetic acid production rates, it is necessary to control the pH of the fermentation broth and in accordance with this invention, the pH can be maintained at a level close to the optimum for the growth of the microorganisms in the broth by neutralizing the dilute acetic acid produced by the fermentation with a special calcined dolomite which has been calcined at a lower temperature than that normally used to produce calcined dolomite. This special calcined dolomite has been found to react with acetic acid leaving unreacted material rich in calcium.

Figure 1:
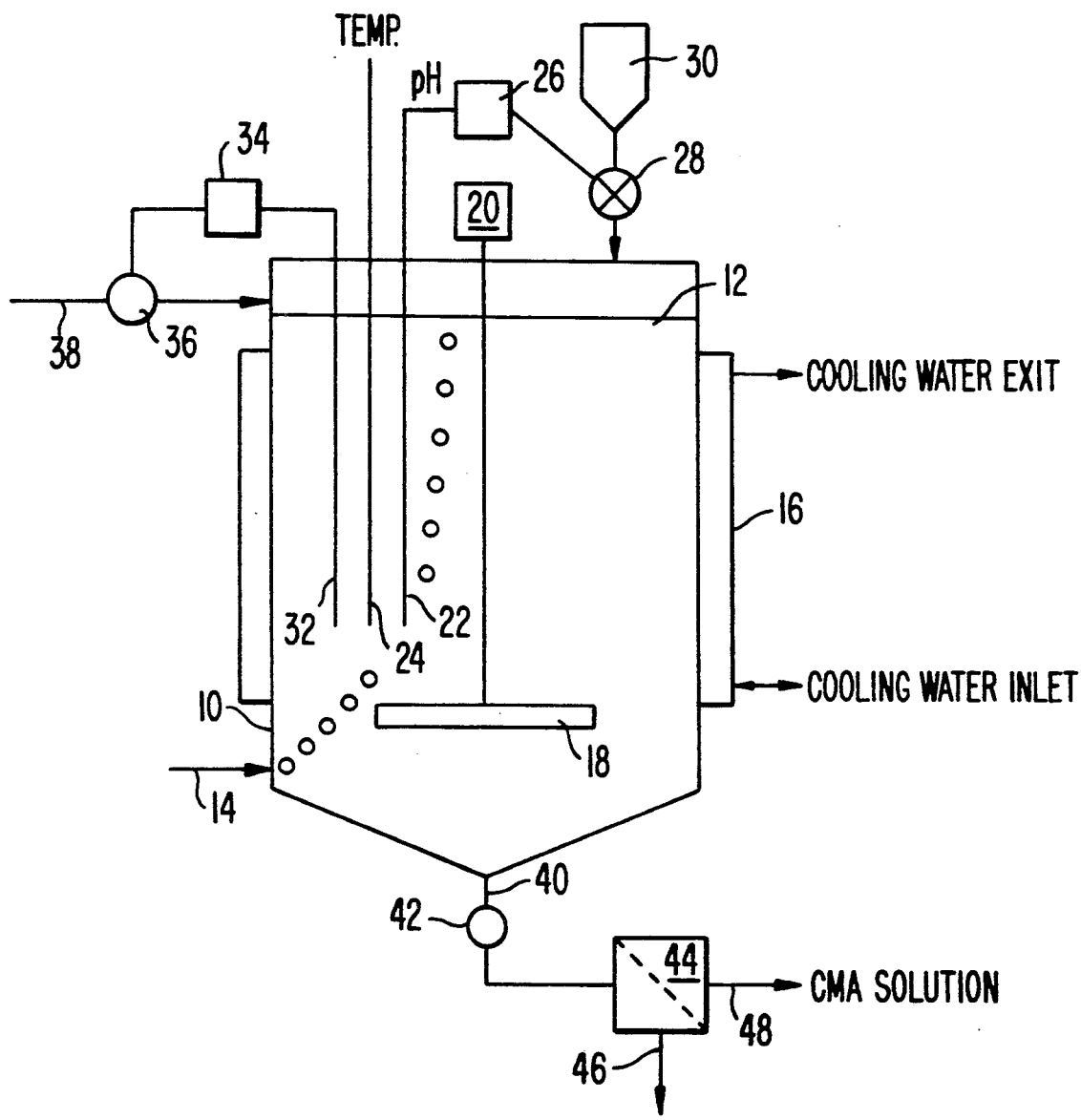
FIG. 1 is a sectional diagrammatic view of a stirred tank batch fermentor with a solids feeder to meter $CaCO_3 \cdot MgO$ to control pH.
Figure 2:
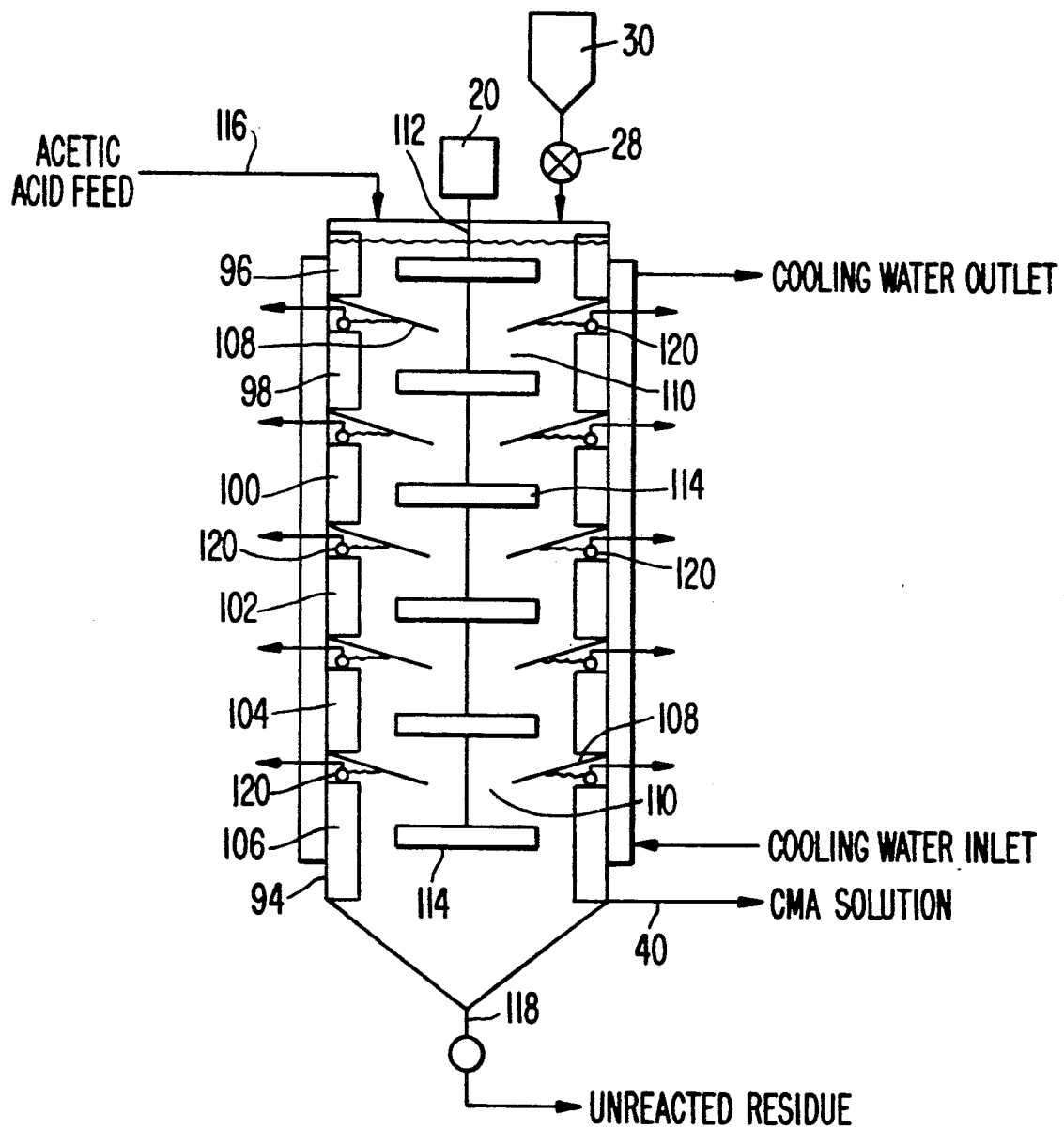
FIG. 2 is a sectional diagrammatic view of a cascade reactor with rotating mixing elements and vertical baffles to promote mixing, a solids feeder to meter $CaCO_3 \cdot MgO$ and gas separators on each stage to separate $CO_2$ formed during the neutralization reaction with acetic acid.

High magnesium dolime is widely available in many snow-belt states with a Mg-to-Ca ratio approaching one. However, the reactivity of MgO in dolime is much lower than the CaO, and the unreacted MgO must be recycled to contact fresh acid in order to react. Production of CMA with a Mg/Ca mole ratio larger than one would require addition of MgO, which is much more expensive than dolime. This is avoided in accordance with this invention by use of the selectively calcined dolomite, largely $MgO.CaCO_3$, made by low-temperature steam calcining. The MgO in selectively calcined dolomite is reported to be more reactive than the MgO in dolime; and by providing the proper calcined dolomite, excess $MgO.CaCO_3$ can be reacted with acetic acid to form CMA of 2.3 Mg:Ca mole ratio while leaving a residue rich in $CaCO_3$. Such a concept could be applied with vinegar that contained 5-30% acetic acid by use of a continuous cocurrent cascade reactor with special check valves in each stage to continuously separate the $CO_2$ gas formed from the vinegar solution (FIG. 2). For thermophilic fermentations with such bacteria as *C. thermoaceticum* the CMA would be produced concurrently with the fermentation by use of conventional fermentors such as depicted in FIG. 1.

Since the chief raw materials for this product, corn and dolomite are widely distributed within the snow belt. CMA could be produced in decentralized processing plants near the source of raw materials and near the major areas of deicer use. Thus, transportation costs are minimized. CMA could be produced more economically if applied as a liquid concentrate instead of as a solid, thus avoiding the handling, storage, distribution and spreading problems associated with a solid CMA product. Use of a liquid concentrate would avoid the costs of drying and consolidating the solid into uniformly sized particles of the shape needed for spreading uniformly as a deicer. The liquid CMA would be more stable in storage than the solid, which tends to absorb $CO_2$ from the atmosphere and be converted to an insoluble carbonate salt with the release of acetic acid, which causes a pervasive vinegar-type odor. The liquid CMA product would also be faster acting than the solid. Since CMA is non-corrosive to steel, the liquid concentrate could be stored and pumped with inexpensive equipment constructed of mild steel alloys.

Samples of various lime products which may be used include dolomite of different screen mesh sizes ($+4$, $-4/+10$, $-10/+30$, $-6/+16$, $-16/+30$ and $-30$), Kemidol oxide fines (dolime). Kemidol hydrate (type N and type S). An experimental calcining procedure included placing samples of lime products in evaporating dishes in a muffle furnace (Hevi-Duty Electric Co., cavity: 8 in wide, 5 in high, 14 in deep) equipped with a type K thermocouple and temperature controller (0°–1000° C.). Carbon dioxide (500 ml/min) was sparged into boiling water and through a 6 mm diameter stainless steel tube into the muffle furnace. Samples were weighed before and after calcining with an electronic balance (0.01 g sensitivity) to determine mass changes during calcining and subsequent cooling in humidified $CO_2$. The volume of water evaporated with the $CO_2$ was measured periodically. Some samples of the calcined dolomite were ground in a Mikro-Sampmill (Pulverizer Machinery Co., Summit, N.J.) equipped with a screen with 0.51 mm diameter holes.

The inorganic constituents of a fermentation broth were simulated for a *C. thermoaceticum* fermentation that had generated 0.25 eq./L of acetic acid (4.55 pH) and consisted of 7.50 g/L $NaHCO_3$, 7.00 g/L $K_2HPO_4$, 5.50 g/L $KH_2PO_4$. 1.00 g/L $(NH_3)_2SO_4$, and 15.00 g/L $CH_3COOH$. Other simulated broths were prepared with 15 g/L acetic acid and with 1, 2, 4, and 8% CMA (2.3 Mg/Ca mole ratio) added to simulate fermentation broths in which the acetic acid had been converted to CMA. Sodium carbonate was added to adjust pH to 5.0. Other solutions that contained 5 to 21% acetic acid in water were neutralized with selectively calcined dolomite to determine Mg/Ca ratio of the dissolved CMA.

Lime products were added to simulated fermentation broths or acetic acid solutions at room temperature and mixed by use of varying levels of agitation. Temperature and pH were measured with some neutralizations as a function of time. The highest level of mixing was obtained with a 1-L Osterizer blender, operated at low speed. Other experiments were conducted with 450 ml of solution in a 600 ml beaker with a rapidly rotating magnetic stirrer or with 600 ml of solution in a 1-L beaker (10- cm i.d.) equipped with four baffles (0.85 cm) and mixed with a LabMaster II Model TS 2510 mixer equipped with a 3.81 cm diameter R-100 turbine impeller (Mixing Equipment Co., Avan, N.Y.). pH was measured with a model PHM 64 meter (Radiometer. Copenhagen, Denmark). Temperature and pH were recorded with a model DC-12 Dianachart (Dianachart Inc., Rockaway, N.J.).

Conductivity of aqueous dispersions of lime products was measured with a model 1481-00 digital conductivity meter (Cole-Parmer Instrument Co.). The method was calibrated with solution's of CaO in water. Concentrations of calcium and magnesium in solutions were measured by a Model AA-6 atomic absorption spectrophotometer (AAS) (Varian Techtron) using an air-acetylene flame. Standards were prepared, each with 25 ppm Ca or Mg, and all solutions contained 1% Lanthanum as release agent.

A test of low-temperature calcination of dolomite in air was conducted under conditions at which selective calcination was reported to occur, 2 hours at 750° C. Different size samples of dolomite of two mesh sizes (−10/+30 and −30) were calcined with results presented in Table 1. For the −30 mesh size, mass loss during calcining varied from 21.4% with 0.1% CaO formed for the largest size sample to 31.7% mass loss with 10.5% CaO for the smallest. The same trend was observed for the −10/+30 mesh dolomite, except for a marked effect of the position sampled within the evaporating dish with the largest sample. A large amount of CaO formed in the upper layer (8.0%) where air circulation would have tended to remove $CO_2$ as formed, compared with the lower layer (0.2% CaO), where the $CO_2$ would not have diffused into the air as readily. This suggested that all the $MgCO_3$ had dissociated to MgO and $CO_2$ in all the samples, and the $CaCO_3$ was beginning to dissociate where the $CO_2$ concentration was lowest.

TABLE 1

Effect of sample size in low-temperature calcining (750° C., 2 hr) of dolomite in air

| Screen Size | Sample Size, g Initial | Sample Size, g Final | Mass change, % | Position Sampled | CaO % |
|---|---|---|---|---|---|
| −10/+30 | 21.2 | 14.4 | −32.2 | mixed | 8.6 |
| −10/+30 | 75.0 | 53.9 | −28.1 | mixed | 7.2 |
|  |  |  |  | upper | 8.0 |
| −10/+30 | 217.4 | 163.0 | −25.0 | middle | 1.0 |
|  |  |  |  | lower | 0.2 |
| −30 | 15.9 | 10.8 | −31.7 | mixed | 10.5 |
| −30 | 49.8 | 38.6 | −22.6 | mixed | 0.2 |
|  |  |  |  | upper | 0.1 |
| −30 | 136.8 | 107.5 | −21.4 | middle | 0.1 |
|  |  |  |  | lower | 0.1 |

The effect of low-temperature calcination of samples of dolomite, dolime and hydrated dolime in wet $CO_2$ is presented in Table 2. Dissociation of $MgCO_3$ occurred with wet $CO_2$ under the conditions reported for low-temperature steam calcination. In addition, the lime products absorbed $CO_2$ and increased in mass until almost all the CaO had been converted into $CaCO_3$.

TABLE 2

Effect of calcining (640° C., 2½ hr) in wet $CO_2$

| Material | Formula | Mass Change, % | CaO Content, % Before | CaO Content, % After |
|---|---|---|---|---|
| Dolomite, −10/+30 mesh | $CaCO_3 \cdot MgCO_3$ | −22.7 | 0 | 0.1 |
| Dolomite, −30 mesh | $CaCO_3 \cdot MgCO_3$ | −22.0 | 0 | 0.1 |
| Kemidol oxide fines (dolime) | $CaO \cdot MgO$ | +38.1 | 51 | 1.8 |
| Kemidol hydrate (type N) | $Ca(OH)_2 \cdot MgO$ | +13.7 | 43 | 1.1 |
| Kemidol hydrate (type S) | $Ca(OH)_2 \cdot Mg(OH)_2$ | +3.6 | 38 | 0.9 |

The composition of two mesh sizes of dolomite is presented in Table 3, calculated from the analyses for Ca and Mg. Also shown are mass changes for low-temperature calcination of samples of dolomite of different mesh sizes. The −30 mesh sample was lower in Mg content than the −10/+30 sample, which was consistent with the mass changes during calcining. The −30 mesh size dolomite was reported by USG Company to contain more impurities, including approximately 1% strontium carbonate, which is more stable than $CaCO_3$ and would not have dissociated during low-temperature calcination.

TABLE 3

Composition of dolomite of different particle sizes and mass loss during selective calcination

| Size Mesh | $CaCO_3$ % ± SEM* | $MgCO_3$ % ± SEM* | Mg/Ca Mole Ratio | Calcining mass change No. Spls. | Calcining mass change % ± SEM* |
|---|---|---|---|---|---|
| −6/+16 | — | — | — | 4 | −22.8 ± 0.1 |
| −10/+30 | 57.2 ± 0.5 | 44.4 ± 1.0 | 0.92 | 4 | −22.6 ± 0.1 |
| −16/+30 | — | — | — | 6 | −22.5 ± 0.2 |

TABLE 3-continued

Composition of dolomite of different particle sizes and mass loss during selective calcination

| Size Mesh | CaCO3 % ± SEM* | MgCO3 % ± SEM* | Mg/Ca Mole Ratio | Calcining mass change No. Spls. | % ± SEM* |
|---|---|---|---|---|---|
| −30 | 56.4 ± 1.2 | 42.6 ± 0.7 | 0.90 | 17 | −21.8 ± 0.0 |

*SEM is Standard Error of the Mean

NEUTRALIZATION TESTS

The process makes primary use of readily available strains of thermophilic acetogenic bacteria that ferment sugars to acetic acid with 100% theoretical yield, instead of the well known Acetobacter (vinegar) process in which the maximum possible yield is only 67% acetic. However, the process is applicable for vinegar and has been used with vinegar made from grain ethanol of 12% acetic acid concentration and with other solutions of acetic acid that simulate vinegar products.

Dolomitic and magnesium lime products of different grades and from various sources (carbonates, oxides and hydroxides) were reacted with simulated fermentation broths containing nutrients, acetic acid and CMA to determine rates of reaction and products formed. Results were obtained to indicate the least expensive route to control pH for optimum production of acetic acid while producing a high concentration of CMA with the desired Ca:Mg ratio in batch, semicontinuous and continuous thermophilic fermentations conducted at 50° to 60° C.

EXAMPLE 1

Results of neutralizations of simulated $C.$ $thermoaceticum$ fermentation broths with −30 mesh dolomite, with hydrated dolime and with low-temperature calcined dolomite are presented in Table 4. The dolomite did not react during mixing for 3 hours. The hydrated lime reacted quickly and the $Ca(OH)_2$ dissolved preferentially to the $Mg(OH)_2$, resulting in a Mg/Ca mole ratio of 0.25 for the dissolved CMA. The calcined dolomite reacted less rapidly, but produced a CMA solution with a Mg/Ca mole ratio of 19.

TABLE 4

Neutralization of simulated $C.$ $thermoaceticum$ fermentation broth with lime products[a]

| Product | Weight added, g | Δt °C. | Time min. | Mg % | Ca % | Mg/Ca mole ratio |
|---|---|---|---|---|---|---|
| Dolomite CaCO3.MgCO3 | 10.91 | 0.0 | No reaction in 3 hours | | | |
| Hydrated dolime Ca(OH)2.Mg(OH)2 | 7.71 | 2.3 | 3 | 0.012 | 0.081 | 0.25 |
| Calcined dolomite CaCO3.MgO | 8.37 | 1.6 | 45 | 0.069 | 0.006 | 19 |

[a]450 g of broth with dissolved nutrients, magnetic stirrer.

EXAMPLE 2

Referring to Table 5, a series of neutralizations was carried out to simulate the broth from a semicontinuous $C.$ $thermoaceticum$ fermentation after several successive additions of $CaCO_3.MgO$. Each solution contained 0.25 eq./L of acetic acid initially and was buffered to pH 5.0 by additions of $Na_2CO_3$ before starting. The time was recorded for pH to rise from 5.0 to 7.0, and the undissolved residue was recovered and analyzed. The rate of neutralization was highest for the 1% CMA solution, 0.068 eq./L-min and decreased to 0.013 eq./L-min for the solution with 8% CMA. The insoluble residue was richer in Ca than Mg, varying from a Mg/Ca mole ratio of 0.55 for 1% CMA solution to 0.19 for the 8% CMA solution, indicating that MgO had reacted preferentially to $CaCO_3$ and the difference increased markedly with increasing CMA content.

TABLE 5

Neutralization of simulated $C.$ $thermoaceticum$ broths with added CMA[a]

| CMA % | 1 | 2 | 4 | 8 |
|---|---|---|---|---|
| Initial pH | 4.25 | 4.30 | 4.78 | 5.03 |
| Na2CO3 needed to reach 5.0 pH, eq./L | 0.155 | 0.139 | 0.080 | — |
| Acetic acid remaining, eq./L | 0.095 | 0.111 | 0.170 | 0.250 |
| Neutralization time, m | 1.4 | 2.0 | 4.2 | 19. |
| Neutralization rate, eq./L-min | 0.068 | 0.056 | 0.040 | 0.013 |
| Residue recovered, g/L | 19.2 | 16.6 | 15.2 | 11.7 |
| Residue analysis | | | | |
| Ca, % | 28.2 | 27.4 | 29.3 | 33.2 |
| Mg, % | 9.4 | 8.0 | 6.6 | 3.8 |
| Mg/Ca mole ratio | 0.55 | 0.48 | 0.37 | 0.19 |

[a]450 g of broth containing 0.25 eq./L of acetic acid in a 600 ml beaker with a magnetic stirrer reacted with 0.52 eq. of CaCO3.MgO.

EXAMPLE 3

Referring to Table 6, rapid neutralization tests were conducted with aqueous solutions of acetic acid of 5.6 to 20.6% with an excess of $CaCO_3.MgO$ in a 1-L Osterizer blender. These results show that as the total dissolved Mg and Ca increased with the higher acid concentrations, the Mg/Ca mole ratio also increased. This finding agrees with the results of Table 5, that the higher the dissolved CMA content, the greater the tendency for MgO to dissolve preferentially to $CaCO_3$.

TABLE 6

Neutralization of acetic acid solutions with selectively calcined dolomite[a]

| Acetic acid, % | Mg % | Ca % | Total % | Mg/Ca mole ratio |
|---|---|---|---|---|
| 5.6 | 0.65 | 0.76 | 1.41 | 1.39 |
| 13.0 | 1.76 | 1.60 | 3.36 | 1.82 |
| 20.6 | 2.99 | 2.02 | 5.01 | 2.45 |

[a]120 ml of solution in a 1-L Osterizer blender at low speed. 2.3 eq. CaCO3.MgO/eq. acetic acid.

Figure 3:
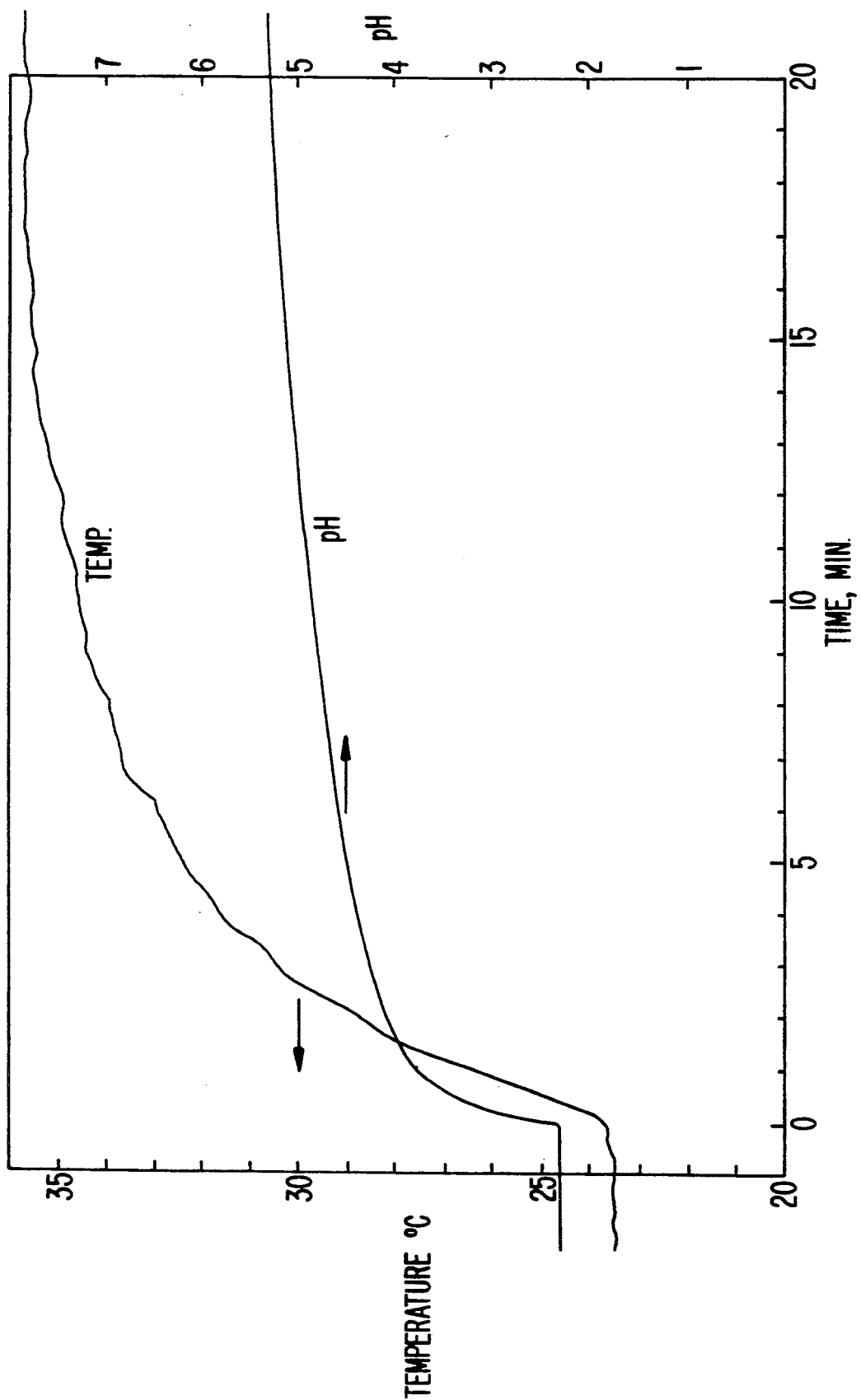
FIG. 3 is plot of temperature and pH versus time for neutralization of 1 equivalent of 10% (W/V) acetic acid with 2 equivalents of $CaCO_3.MgC$.

FIG. 3 shows the neutralization curve for 600 ml of 10% (w/v) acetic acid (1 eq.) mixed at 1600 rpm in a 1000 ml beaker with baffles. Two eq. of $CaCO_3.MgO$ of a size range, −12/+14 mesh, was added and pH and temperature were recorded. Considerable foaming indicated that some $CaCO_3$ was dissolving. The temperature increased rapidly at the beginning and peaked after 17 min with a temperature rise of 12.2° C. pH increased from 2.31 initially to 5.2 after 17 min and increased linearly afterward. The linear increase may have been caused by attrition of the particles of calcined dolomite at the high mixing speed, and it is preferable to conduct mixing at as low a speed as possible to avoid particle breakup of the calcined dolomite. The final CMA solution, which was centrifuged to remove suspended solids, had a distinctly yellowish tint from impurities such as $Fe_2O_3$ dissolved from the $CaCO_3.MgO$.

EXAMPLE 4

Table 7 shows results of neutralizing 600 ml of grain vinegar of 11.6% (w/v) acetic acid (1.16 equivalents) mixed at 300 rpm in a 1000 ml beaker with baffles. The beaker was wrapped with ½ in. thickness of flexible plastic foam insulation to reduce heat loss; and a few drops of Hodag FD-62 silicone-based antifoam agent were added to reduce foam caused by evolution of $CO_2$ from dissolution of $CaCO_3$. The initial temperature and pH were 21° C. and 2.2, respectively. 138 g or approximately 3.3 equivalents of $CaCO_3$, MgO of size range −16/+20 mesh were added, pH and temperature were recorded and 1 ml samples were withdrawn at the times listed in Table 7 for analysis. The Mg and Ca concentrations were used to calculate the Mg:Ca mole ratio and the of acetic acid reacted in each sample. The maximum temperature rise was 28° C. after 20 min., and temperature then gradually decreased as the rate of heat dissipation exceeded the rate of heat generated from the neutralization reaction. The concentration of Ca reached a maximum after 26 min., when 94% of the acetic acid had been reacted, and Ca declined in succeeding samples. The Mg:Ca mole ratio continued to increase throughout the test, reaching a maximum of 4.1 after 105 min.

The reacted contents of the beaker were screened to remove a solid residue of +40 mesh size and centrifuged to separate smaller particles of unreacted residue from the water-clear solution of 14.3% CMA (w/v). After rinsing with distilled water and drying to constant weight in air at room temperature, 113.4 g of +40 mesh size and 0.6 g of −40 mesh fines were recovered. A material balance calculation based on the composition of the original dolomite obtained from USG Co., Genoa. Ohio (Mg:Ca mole ratio of 0.92, 1.5% impurities such as $Al_2O_3$, $SiO_2$ and $Fe_2O_3$), and the masses of selectively calcined dolomite ($CaCO_3$ . MgO) and unreacted residue showed that the unreacted residue was enriched in Ca with a Mg:Ca mole ratio of 0.49. The air-dried +40 mesh residue was evaluated for mass loss during heating under vacuum as an indication of the amount of adsorbed volatiles. The mass loss after heating for 16 hr. in a vacuum oven at 25° C. was 1.8%. A similar test with a sample of the −16/−20 mesh size selectively calcined dolomite that had been wet with distilled water and air dried was 0.7%. The color of the smallest particle size residue was reddish tan from the impurities such as $Fe_2O_3$ that had been dissolved from the $CaCO_3$ . MgO at low pH and precipitated from solution as a result of increasing pH above 7.

TABLE 7

Neutralization of Vinegar with $CaCO_3.MgO$

| Time min. | pH | Temp. °C. | Mg % | Ca % | Mg/Ca mole ratio | Acid reacted % |
|---|---|---|---|---|---|---|
| 1 | 3.3 | 25 | 0.28 | 0.24 | 1.9 | 18 |
| 2 | 3.7 | 28 | 0.48 | 0.36 | 2.2 | 29 |
| 3 | 3.9 | 30 | 0.69 | 0.47 | 2.4 | 41 |
| 5 | 4.3 | 33 | 0.95 | 0.64 | 2.5 | 56 |
| 10 | 4.7 | 37 | 1.33 | 0.78 | 2.8 | 76 |
| 15 | 5.0 | 39 | 1.51 | 0.81 | 3.1 | 84 |
| 26 | 5.4 | 39 | 1.71 | 0.85 | 3.3 | 94 |
| 36 | 5.6 | 38 | 1.76 | 0.79 | 3.7 | 95 |
| 54 | 6.1 | 35 | 1.85 | 0.79 | 3.9 | 98 |
| 105 | 7.5 | 30 | 1.92 | 0.76 | 4.1 | 100 |

The practical application of the above described method for the preparation of calcium magnesium acetate (CMA) from acetogenic fermentation broths or acetic acid solutions may be accomplished using various production techniques and devices. In general, the methods may be applied directly to the fermentation broth during acetogenic fermentations in order to optimally control the cell growth without the risk of using highly caustic or alkaline CaO while producing CMA enriched in magnesium. Alternatively, a cascade reactor with rotating mixing elements and gas separating baffles, as shown in FIG. 2, may be applied to fermentation broths which are pumped to the cascade reactor and recycled back to a fermentor. Also, the cascade reactor may be applied to aqueous or nonaqueous solutions of acetic acid, however produced, some of which have been separated or concentrated from the fermentation broths by such methods as: use of filters, membranes, centrifuges or the like to effect a physical separation of substantially all the insoluble particulate matter from the broth or, use of methods to separate and/or concentrate a large portion of the acetic acid from the other soluble and insoluble components of the broth, i.e., liquid-liquid extraction, freeze concentration, crystallization, selective membrane processes.

More specifically, several types of processes may be used in conjunction with a fermentor and/or a reactor to ensure continuous fermentation and production of CMA. For example, &:he type of process used may be either a batch or fixed bed process, or a continuous process operated with either cocurrent or counter current flow of the liquid with respect to the solid stream.

Shown in FIG. 1 is one such batch fermentor which includes an enclosed fermentation tank 10 in which a sterile fermentation medium 12 is rendered anaerobic by purging with $CO_2$ from an inlet 14 to remove the oxygen, and inoculated with the desired strain of bacteria. Temperature is controlled to the desired level, 50°-60° C., for most thermophilic bacteria such as *Clostridium thermoaceticum* by means of recirculating hot water through an external cooling jacket 16 mounted on the tank 10. An agitator 18 driven by an agitator drive motor 20 is used to mix the contents, and one or more probes 22,24 are used to monitor temperature and pH. As the fermentation process progresses, the bacterial cells grow and produce acetic acid which decreases the pH. A pH controller 26 activates a solids feeder 28 to meter specified amounts of $CaCO_3$ . MgO from a hopper 30 into the fermentor at a rate which maintains the pH in the optimum range for both rate of growth and acetic acid production, which is between pH 5 and pH 7 for most thermophilic bacteria. The $CaCO_3$. MgO may be metered as a granular solid or added as a slurry of finely ground particles in water, as long as it contains no free oxygen. A sensor 32 is used to monitor nutrient level in the broth and a controller 34 activates a pump 36 to add nutrients such as corn starch hydrolysates into the fermentor as needed through a nutrient feed inlet 38.

Gases such as CO, $CO_2$ and $H_2$ are added as additional nutrients that also ensure anaerobic conditions until fermentation is complete and the batch is discharged from the bottom of the fermentor discharge outlet 40 and an outlet control valve 42 to pass through a separator 44 to remove the bacterial cells and unreacted $CaCO_3$ . MgO residue from the CMA solution. The unreacted residue passes through a separator outlet 46 and the CMA solution passes through an outlet 48 to then be concentrated by evaporation and, optionally, dried to form solid CMA.

The apparatus of FIG. 1 is also applicable for vinegar fermentations with Acetobacter, except that ethanol instead of a sugar such as glucose is the substrate that is converted into acetic acid, and air or oxygen gas must be continuously supplied to the fermentor instead of the inert or reducing gases used for thermophilic bacteria. Cooling water is also required to remove the heat generated by the partial oxidation of ethanol to acetic acid.

The apparatus of FIG. 1 can also be operated as a single stage continuous stirred tank fermentor in which a nutrient feed is pumped in through nutrient feed inlet 38 at a constant rate and an effluent stream containing both a dilute CMA solution and unreacted nutrients is continuously removed. For a continuous system to convert essentially all the carbohydrate in the feed stream into acetic acid, a number of stirred tank fermentors in series are required. In this design, the effluent stream from one fermentor becomes the feed stream to the next fermentor.

As shown in FIG. 2, an alternate and preferred continuous reactor for reacting solutions of acetic acid with selectively calcined dolomite includes a cascade reactor having an enclosed tank 94 separated into vertically arranged compartments 96-106 by downwardly inclined conical baffles 108 mounted on the inner wall of the tank. Each compartment includes vertical baffles 109 mounted on the inner wall of the tank 94 which can be spaced around the inner wall between the baffles 108. Each vertical baffle extends into the tank for a distance at least equal to 1/12 the diameter of the tank. The baffles 108 each have a central opening 110 at the apex of the conical baffle to pass effluent between chambers and to receive a central rotating shaft 112 for mixing elements 114 positioned in each compartment. The baffles also provide a means for separating $CO_2$ gas from the liquid in each compartment. Acetic acid solution is introduced through an inlet 116 and $CaCO_3$ MgO is also introduced in cocurrent flow through the top of the reactor, the two being introduced at the proper rates to ensure the desired composition of liquid leaving the reactor at the bottom. A typical desired composition is usually a solution with a 7:3 Mg:Ca mole ratio, except in some cases it may be desirable to achieve the highest Mg:Ca ratio that can be obtained. It is obvious that the reactor could be operated in countercurrent flow for certain applications. Unreacted solid residue that settles to the bottom of the fermentor is continuously removed via an outlet 118. A means for removing $CO_2$ formed from the reaction of $CaCO_3$ with acetic acid includes the conical shaped baffle 108 positioned at the top of each compartment and inclined at an angle such that the flow of solids is not impeded while most of the $CO_2$ gas formed in each compartment is trapped by the inverted conical baffle. The trapped $CO_2$ gas exits through duct valves 120 at the top of each compartment. The duct valves are the conventional design, consisting of a hollow sphere that is held in the closed position by the buoyant force of the sphere floating in the liquid and pressing against the valve seat orifice when the system is filled with liquid. As a sufficient amount of $CO_2$ gas is trapped in the compartment, the liquid level in the duct valve decreases to a point where the buoyant force becomes zero. At this point, the valve opens under the influence of gravity to release some of the $CO_2$ gas.

What is claimed:

1. A process for preparing magnesium-enriched calcium magnesium acetate by reacting selectively calcined dolomite ($CaCO_3$ MgO) formed by selective calcination at temperatures within the range of 720°–770° C. in air or 550°–650° C. in inert gas with acid solutions which includes the steps of adding selectively calcined dolomite to the acid solution in an amount in excess of the amount required to react with the acid solution to form calcium magnesium acetate and causing magnesium to preferentially dissolve at a higher rate than calcium to produce a calcium magnesium acetate solution enriched in magnesium and an unreacted residue enriched in calcium.

2. The process of claim 1 which includes separating the calcium magnesium acetate solution from the residue and removing part of the liquid therefrom to prepare a concentrated liquid calcium magnesium acetate product consisting of 30–40% solids, limited in dissolved solids only by the crystallization of a portion of the solids.

3. The process of claim 1 which includes removing substantially all the liquid from the calcium magnesium acetate solution to form solid calcium magnesium acetate.

4. The process of claim 1 which includes removing liquid from said residue to form a highly porous mineral structure consisting of a matrix of $CaCO_3$ with smaller amounts of MgO.

5. The process of claim 1 :;herein the acid is acetic acid.

6. The process of claim 1 which includes producing said acid in a fermentation broth and adding said selectively calcined dolomite to neutralize the acid produced.

7. The process of claim which includes producing said acid by diluting a more concentrated solution to a concentration limited only so as not to exceed the solubility of the calcium magnesium acetate formed from the reaction.

8. The process of claim 6 which includes producing acid by fermentation caused by the introduction of fermentation producing microorganisms into said fermentation broth and adding said selectively calcined dolomite during the fermentation to control the pH of the broth and maintain the pH at a level to allow the growth of the microorganisms and formation of acetic acid in the broth.

9. The process of claim 8 which includes maintaining the fermentation broth at temperatures of 50° to 60° C.

10. The process of claim 8 which includes rendering the fermentation broth a;:aerobic by purging with gases such as carbon monoxide, hydrogen and carbon dioxide.

11. The process of claim 8 which includes providing fermentation producing microorganisms and a fermentation broth which will produce acetic acid during fermentation, and maintaining the fermentation broth at temperatures of 50° to 60° C. during fermentation.

12. The process of claim 11 which includes removing part of the liquid to prepare a concentrated liquid calcium magnesium acetate product consisting of 30-40% solids, limited in dissolved solids only by the crystallization of a portion of the solids.

13. The process of claim 11 which includes removing substantially all the liquid from the calcium magnesium acetate solution separated from the residue to form solid calcium magnesium acetate.

14. The process of claim 13 which includes removing liquid from said residue to form a highly porous mineral solid consisting of a matrix of $CaCO_3$ with smaller amounts of MgO.

15. A method for producing a highly porous, absorbtive mineral solid from dolomite which includes reacting selectively calcined dolomite ($CaCO_3 \cdot MgO$) with an acid solution to cause a large fraction of the MgO to be preferentially dissolved to leave a Ca enriched residue, separating the Ca enriched residue and removing liquid from the residue to form a solid.

16. The method of claim 15 wherein the acid solution is a solution of acetic acid.

17. The method of claim 16 which includes selectively calcining dolomite in the presence of water vapor at a temperature barely high enough to cause $MgCO_3$ to destruct to MgO and $CO_2$ but low enough so as not to substantially affect $CaCO_3$, cooling the calcined product in an atmosphere of humidified $CO_2$ and reacting the resultant calcined dolomite ($CaCO_3 \cdot MgO$) with the acid solution.

18. A process for preparing magnesium-enriched calcium magnesium acetate which includes the steps of selectively calcining dolomite in the presence of water vapor at a temperature barely high enough to cause $MgCO_3$ to destruct to MgO and $CO_2$ but low enough so as not to substantially affect $CaCO_3$, cooling the resultant calcined product in an atmosphere of humidified $CO_2$ to cause any CaO that formed to be converted to $CaCO_3$, reacting the resultant calcined dolomite ($CaCO_3 \cdot MgO$) with an acid solution to cause magnesium to preferentially dissolve at a higher rate than calcium to produce a calcium magnesium acetate solution enriched in magnesium and an unreacted residue rich in calcium and subsequently separating the calcium magnesium acetate solution from the calcium rich residue.

19. The process of claim 18 which includes selectively calcining dolomite in a heated furnace, creating an atmosphere of wet $CO_2$ in the furnace by introducing a $CO_2$-water mixture into the furnace to evaporate water with the $CO_2$.

20. The process of claim 19 wherein said dolomite is heated in said atmosphere of wet $CO_2$ at temperatures within the range of from 550° to 650° degrees centigrade.

21. The process of claim 20 wherein the selectively calcined dolomite is added to the acid solution in an amount in excess of the amount required to neutralize the acid to create said unreacted residue.

22. The process of claim 21 which includes removing liquid from said separated calcium rich residue to form a highly porous mineral structure consisting of a matrix of $CaCO_3$ with smaller amounts of MgO.

23. The process of claim 21 which includes producing said acid solution in a fermentation broth by fermentation caused by the introduction of fermentation producing microorganisms into said fermentation broth and adding said selectively calcined dolomite to the fermentation broth during the fermentation to control the pH thereof.

24. The process of claim 23 which includes mixing said fermentation broth in a fermentor during fermentation and removing during fermentation any gases created by a reaction of $CaCO_3$ with the acid solution.

25. The process of claim 24 wherein said acid solution is an acetic acid solution.

26. A process for preparing magnesium enriched calcium magnesium acetate which includes the steps of heating a dolomitic lime product in a wet $CO_2$ atmosphere at 550°-650° C. for a period sufficient to cause dissociation of $MgCO_3$ to MgO and $CO_2$ and to cause resultant lime products to absorb $CO_2$ and increase in mass to convert CaO to $CaO_3$ to provide calcined dolomite $CaCO_3 \cdot MgO$), adding the resultant calcined dolomite to an acid solution in amounts sufficient to cause magnesium to preferentially dissolve at a higher rate than calcium to produce a calcium magnesium acetate solution enriched in magnesium and an unreacted residue rich in calcium, and subsequently separating the calcium magnesium acetate solution from the calcium rich residue.

27. A process for preparing magnesium enriched calcium acetate which includes the steps of calcining a dolomitic lime product under conditions to convert the $MgCO_3$ content thereof to MgO while leaving the $CaCO_3$ matrix thereof substantially intact, adding the resultant selectively calcined dolomitic product to an acid solution to cause the magnesium therein to preferentially dissolve at a higher rate than the calcium therein to produce a calcium magnesium acetate solution enriched in magnesium, the selectively calcined dolomite product being added to the acid solution in an amount in excess of that required to react with the acid solution to provide an unreacted calcium rich residue.

28. The process of claim 27 wherein said acid solution is an acetic acid solution.

29. The process of claim 27 which includes removing liquid from said calcium magnesium acetate solution and said unreacted calcium rich residue.

30. The process f claim 29 which includes removing sufficient liquid from said residue to form a solid mineral structure consisting primarily of $CaCO_3$.

31. The process of claim 30 which includes removing sufficient liquid from the calcium magnesium acetate solution to form solid calcium magnesium acetate.

32. A process for preparing magnesium enriched calcium magnesium acetate (CMA) by reacting selectively calcined dolomite consisting primarily of $CaCO_3 \cdot MgO$ with lesser amounts of $CaCO_3 \cdot MgCO_3$ and $CaO \cdot MgO$, with acetic acid solution which includes the steps of comixing or admixing either one with the other in amounts that maintain the total chemical equivalents of alkaline earth elements in excess of the chemical equivalents of the acid solution to form CMA and causing magnesium to preferentially react to produce CMA solution with a Mg/Ca mole ratio greater than one (1) and an unreacted residue enriched in calcium.

33. The process of claim 32 which includes separating the CMA solution from the residue and removing part of the liquid therefrom to prepare a concentrated liquid CMA product limited in the concentration of dissolved solids only by the crystallization or formation of a solid phase of a substantial portion of the dissolved solids.

34. The process of claim 32 wherein the acetic acid solution is either aqueous or non aqueous.

35. The process of claim 32 which includes producing said acetic acid in a fermentation broth by fermentation caused by the introduction of acetate producing microorganisms into said fermentation broth and said selectively calcined dolomite during the fermentation to control the pH of the broth and maintain the pH at a level to allow the growth of the microorganisms and formation of the acetic acid in the broth.

36. The process of claim 35 which includes selection of anaerobic microorganisms from one or more strains of thermophilic acetogenic bacteria including *Acetogenium kivui, Clostridium thermoaceticum* or *Clostridium thermoautotrophicum*, and maintaining the fermentation broth at a pH between 5 and 7 and at temperatures at 50° to 60°.

37. The process of claim 35 which includes rendering the fermentation broth anaerobic by purging with gasses such as carbon monoxide, hydrogen and carbon dioxide.

38. The process of claim 35 which includes providing aerobic acetogenic microorganisms selected from one or more strains of Acetobacter or other vinegar-forming bacteria and a fermentation broth which will produce acetic acid during fermentation.

39. The process of claim 35 which includes separating the CMA solution from the bacterial cells and unreacted residue and removing part of the liquid therefrom to prepare a concentrated liquid CMA product limited in concentration of dissolved solids only by the crystallization or separation of a substantial portion of the dissolved solids.

40. The process f claim 39 which includes removing substantially all the liquid from the CMA solution separated from the residue to form solid CMA.

41. The process of claim 39 which includes removing liquid from said residue to form a highly porous mineral solid consisting primarily of a matrix of $CaCO_3$ with smaller amounts of $MgO$.

42. The process of claim 32 which includes the steps of contacting the selectively calcined dolomite and the acetic acid solution until the pH rises above seven (7), separating both the residue of unreacted selectively calcined dolomite and precipitate from the solution of CMA and removing part of the liquid therefrom to prepare a concentrated liquid CMA product limited in the concentration of dissolved solids only by crystallization or formation of a solid phase of a substantial potion of the dissolved solids.

43. The process of claim 42 wherein the magnesium/calcium ratio of the CMA is in the range of 1 to 20.

44. A process for preparing magnesium-enriched CMA which includes the steps of:
  (1) selectively or partially calcining dolomite at a temperature barely high enough to cause most of the $MgCO_3$ to dissociate to $MgO$ and $CO_2$ but low enough so as not to cause substantial calcination of $CaCO_3$, and
  (2) comixing or admixing either one with the other of selectively calcined dolomite and aqueous or nonaqueous solutions or acetic acid in amounts such that the total chemical equivalents of alkaline earth elements exceeds the chemical equivalents of the acid solution to cause magnesium to react preferentially or at a higher rate than calcium to produce a CMA product enriched in magnesium with a magnesium/calcium mole ratio greater than 1 and an unreacted residue enriched in calcium.

45. The process of claim 44 which includes separating the CMA product from the residue and removing part of the liquid therefrom to prepare a concentrated liquid CMA product limited in concentration of dissolved solids only by the crystallization or formation of a solid phase of a substantial portion of the dissolved solids.

46. The process of claim 45 which includes selectively calcining dolomite in a heated furnace, creating an atmosphere of wet $CO_2$ in the furnace by introducing a $CO_2$-water mixture into the furnace to evaporate water with the $CO_2$ during the calcining and during subsequent cooling to cause any $CaO$ formed to be converted to $CaCO_3$.

47. The process of claim 46 wherein said dolomite is heated in said atmosphere of wet $CO_2$ for 1 to 4 hours at temperatures within the range of 550° to 650 degrees Celsius and cooled from the calcination temperature to within the range of 450° to 500 degrees Celsius during a period of 15 to 60 minutes.

48. The process of claim 47 which includes removing liquid from said separated calcium rich residue to form a highly porous mineral structure consisting of a matrix of $CaCO_3$ with smaller amounts of $MgO$.

49. The process of claim 48 which includes producing said acetic solution in a fermentation broth by fermentation caused by the introduction of acetate producing microorganisms into said fermentation broth and adding said selectively calcined dolomite in increments to the fermentation broth during the fermentation to control the pH thereof and react with the said acetic acid at approximately the same rate as the acid is formed.

50. A process for preparing magnesium enriched CMA which includes the steps of heating a dolomitic lime product in a wet $CO_2$ atmosphere at 550° to 650° C. for a period sufficient to cause dissociation of most of the $MgCO_3$ to $MgO$ and $CO_2$ and cooling in a wet $CO_2$ atmosphere to cause a large part of any lime product formed to absorb $CO_2$ and increase in mass to convert $CaO$ to $CaCO_3$ and provide mainly selectively calcined dolomite ($CaCO_3.MgO$), combining the resultant calcined dolomite with acetic acid solution in amounts sufficient to cause magnesium to preferentially react at a higher rate than calcium to produce a CMA solution enriched in magnesium with a Mg/Ca mole ratio greater than 1 and an unreacted residue rich in calcium, and subsequently separating the calcium magnesium acetate solution from the calcium rich residue.

51. A process for preparing magnesium enriched CMA which includes the steps of partially calcining a dolomitic lime product under conditions to convert most of the $MgCO_3$ content thereof to $MgO$ while leaving most of the $CaCO_3$ matrix thereof substantially intact, contacting the resultant partially calcined dolomitic product with an acid solution to cause the magnesium therein to preferentially react at a higher rate than the calcium therein to produce a CMA solution enriched in magnesium with a Mg/Ca mole ratio greater than 1, the total chemical equivalents of alkaline earth elements in selectively calcined dolomite product being present in excess of the chemical equivalents of acid solution to provide an unreacted calcium rich residue.

* * * * *